United States Patent [19]
von Berg

[11] Patent Number: 4,696,305
[45] Date of Patent: Sep. 29, 1987

[54] FLOW CONTROLLER

[75] Inventor: Peter von Berg, Neukeferloh, Fed. Rep. of Germany

[73] Assignee: Peter von Berg Extrakorporale Systems-Medizintechnik GmbH, Munich, Fed. Rep. of Germany

[21] Appl. No.: 876,170

[22] Filed: Jun. 19, 1986

[30] Foreign Application Priority Data

Jul. 15, 1985 [DE] Fed. Rep. of Germany ....... 3525191

[51] Int. Cl.$^4$ .......................... A61M 5/00; F16K 51/00
[52] U.S. Cl. .................................. 128/673; 604/249; 251/117
[58] Field of Search ................ 128/672-673, 128/675; 604/246-249, 256, 236-238, 30, 32-34; 251/117, 333-334

[56] References Cited

U.S. PATENT DOCUMENTS

| 2,649,276 | 8/1953 | Titus | 251/110 |
|---|---|---|---|
| 3,675,891 | 7/1972 | Reynolds et al. | 128/673 X |
| 3,768,514 | 10/1973 | Goto | 251/19 L X |
| 4,090,503 | 5/1978 | Speidel | 73/748 X |
| 4,210,178 | 7/1980 | Morse et al. | 604/249 X |
| 4,245,636 | 1/1981 | Sparks et al. | 604/249 |
| 4,291,702 | 9/1981 | Cole et al. | 128/673 X |
| 4,337,770 | 7/1982 | Young et al. | 604/30 |
| 4,341,224 | 7/1982 | Stevens | 128/673 X |
| 4,381,591 | 5/1983 | Barger et al. | 604/30 X |
| 4,444,198 | 8/1984 | Petre | 604/30 X |
| 4,456,223 | 6/1984 | Ebling | 604/249 X |
| 4,497,468 | 2/1985 | Hubbard et al. | 604/249 X |
| 4,537,387 | 8/1985 | Danby et al. | 604/248 X |
| 4,550,748 | 11/1985 | Nunez | 251/117 X |
| 4,624,662 | 11/1986 | Le | 604/249 |

FOREIGN PATENT DOCUMENTS

| 0009911 | 4/1980 | European Pat. Off. | 604/249 |
|---|---|---|---|
| 0079617 | 5/1983 | European Pat. Off. | 128/672 |

Primary Examiner—William E. Kamm
Assistant Examiner—Angela D. Sykes
Attorney, Agent, or Firm—Helfgoth & Karas

[57] ABSTRACT

A flow control device for use with flowing fluids to monitor pressure during blood pressure measurements having at least one passage extending from an inlet to an outlet. This passage has two flow paths, one a non-closable, narrow flow path including a capillary bore for normal flow. The other is a flushing chamber having a larger crossectional opening which is closable by a rapid flush valve. The rapid flush valve includes a valve body made of elastically deformable material and disposed in the flushing chamber. The valve body may be stretched by a plunger which thereby reduces its crossection. In the normal position, the outside of the valve body contacts the wall of the flushing chamber and blocks the flow path through the chamber. If the plunger is depressed, the valve body is deformed elastically, elongating it to thereby reduce its crossection and spacing it from the walls of the flushing chamber. This opens the flow path through the flushing chamber.

14 Claims, 2 Drawing Figures

FLOW CONTROLLER

BACKGROUND OF THE INVENTION

The invention relates to a flow control device for use with flowing liquids to monitor pressure during blood pressure measurements. Flow controllers of this type are known, for example, from DE Patent No. 30 23 345 or U.S. Pat. No. 4,341,224.

In general, during continuous intravasal pressure measurements, care must be taken that no blood coagulation occurs at the tip of the needle. This is achieved by producing continuous flushing. The needle is kept open by the flow of a fluid from a pressurized flushing fluid container and dispensed by the flow control device. The quantity of flushing fluid normally flowing is determined by a capillary bore and is commonly in the range of 3–6 ml/hour.

To prevent both a hazard to the patient and falsification of the results, the entire measuring system must be absolutely free of air bubbles, i.e., it must be ble of air before being connected to the patient. This is achieved by providing for a separate closable passage for the flushing fluid which has a considerable larger cross-sectional opening than has the capillary bore. As long as this closable passage is open, the flushing fluid flows through the passage which has a larger cross-section and thus fills the entire system in a short time. After the passage is closed, however, only the amount of flushing fluid which can pass through the capillary bore enters the system. In the flow control device described in DE Patent No. 30 23 435, the valve body which closes the passage is sealed by an O-ring with respect to a valve seat in the housing when in its inactive position. The capillary bore is contained in an insert within the valve body which has a passage upstream of the capillary bore in fluid flow communication with the inlet of the device.

A separate spring urges the valve body into its closed position. The valve is opened when the valve body is displaced against the force of that spring.

A similar flow control device, is shown in U.S. Pat. No. 4,497,468 and U.S. Pat. No. 4,291,702 in which the valve body is also disposed opposite a valve seat in the housing.

U.S. Pat. No. 3,675,891 also shows a similar flow control device in which the closable passage having the greater crossection for the capillary bore is disposed in parallel with the bore, serving as a bypass. Here too, to close the passage, a valve body is resiliently pressed against a valve seat in the housing. To open the passage for rapid flushing, the valve body must be raised from the valve seat against the force of the valve body acting as a spring, as in the previous examples.

Generally, it should be noted that the known flow control devices as well as those according to the present invention are intended for a single use only. Thus, they must be capable of being manufactured cost effectively but yet must function perfectly, making great demands on the tightness of the valve seat of the closable passage.

These demands have not as yet been met satisfactorily in the described state of the art. The known devices are generally composed of many individual parts, some of which are difficult to make and for a single use device are still too costly.

SUMMARY OF THE INVENTION

It is an object of the present invention to provide an improved flow control device of the above-described kind with simpler construction while still functioning accurately and reliably.

Another object of the present invention is to provide a flow control device by having an elastically deformable valve body in the closable passage of the device which becomes distended when a plunger extends into the valve body, thereby reducing the diameter of the valve body and resulting in the opening of the passage.

A further object of the present invention is to shape the elastic valve body so that it will stretch when the "rapid flush valve" of the flow control device is actuated, thereby opening the flow passage. Prior to flushing, the same elastic properties of the valve body are used to keep the valve in its closed position without requiring an additional spring.

Yet another object of the present invention is to provide a flow control device having a valve with a valve seal where no great demands are made on the surface quality of the valve seat even if it may have a large surface area. The valve body is made of elastic deformable material so that any surface unevenness in the seal would be compensated by the elastic deformation of the valve body material.

These and other objects, features and advantages of the invention will, in part, be pointed out with particularly, and will, in part become obvious from the drawings which form an integral part thereof.

BRIEF DESCRIPTION OF THE DRAWING

In the drawing.

In the various figures of the drawing like reference characters designate like parts.

DESCRIPTION OF THE PREFERRED EMBODIMENT

Figure 1:
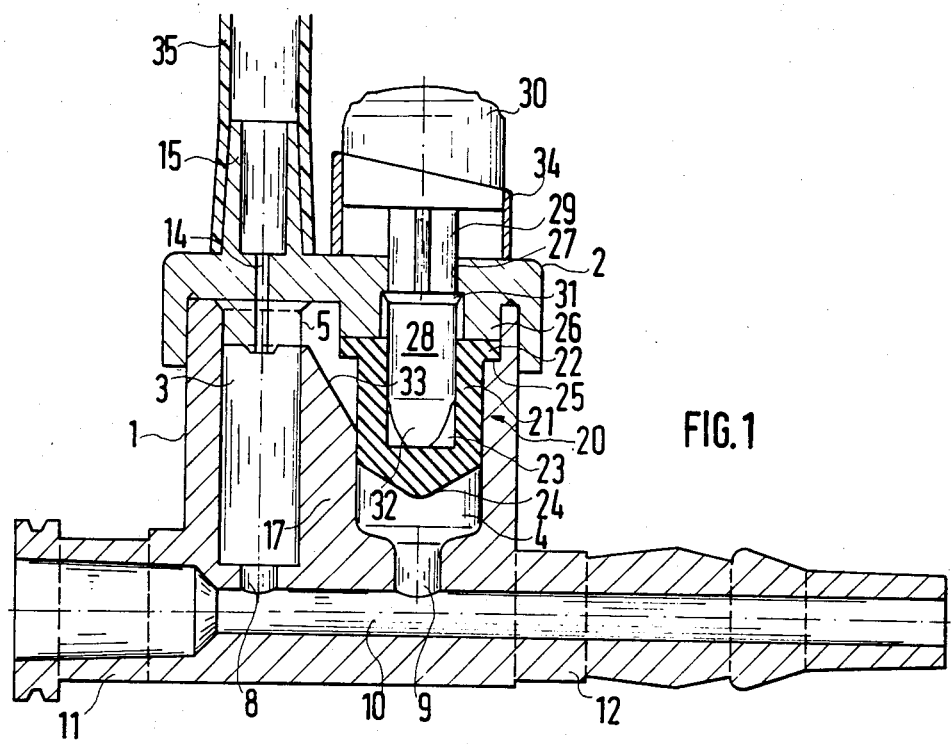
FIG. 1 is a crossectional view of the flow control device according to the present invention showing the normal position when the rapid flushing passage is closed.

Referring to the drawing, the flow control device has a housing 1 closed by a cover 2. In the interior of the housing are provided two substantially cylindrical and mutually parallel chambers 3 and 4 that communicate with each other through a connecting passage 5 at the upper ends of chambers 3 & 4. Chamber 3 provides a narrow, non-closable flow passage while chamber 4 forms the closable rapid flushing passage. Chamber 3 contains a glass tube 6 with a very narrow capillary opening. At their lower ends, both chambers 3 and 4 have respective openings 8 and 9 that terminate in a channel 10. Channel 10 lies transverse to the main direction of the chambers 3 and 4 and both ends of channel 10 terminate in connectors 11 and 12, respectively, which are integral with the housing.

Connector 11 is the inlet and would be mated with a pressure transducer (not shown) which would be sealed by a diaphragm in a fluid-tight connection to channel 10. Attached to the outlet connector 12 would be a tube (not shown), connected by way of example by a push-on fit, and leading to the patient. The tube would typically carry a canula tip at its free end.

Opposite chamber 3, cover 2 has a cylindrical plug 13 extending into the upper end of the chamber 3. This plug has a passage 14 which extends completely through the cover and is aligned with the capillary bore 7. The passage 14 terminates at the outside of the cover 2 in an inlet connector 15 formed integral with cover 2 which is adapted to received a tube 35 coupled to a flushing fluid container (not shown), if necessary via a drip chamber.

The plug 13 has a lateral opening 16 transverse to the passage 14 and in flow communication therewith. Lateral opening 16 is flush with respect to the passage 5 formed in wall 17 that separates the two chambers 3 and 4.

The glass tube 6 is sealed with respect to the bottom of the plug 13 by a sealing ring 18 so that fluid can pass from the passage 14 only into the capillary bore 7 but not into the remaining space of the chamber 3. Similarly, the lower end of the glass tube 6 is retained at the bottom end of the chamber 3 by a sealing ring so that fluid can pass out of the capillary bore 7 only through opening 8.

Located in the chamber 4 is a closable rapid flush valve 20 having a valve body 21 made of an elastic material such as silicon rubber or other rubber. The valve body 21 has a substantially cylindrical shape. At its upper end here is a redially outwardly extending flange 22. An internal cylindrical bore 23 is provided with the bore being open in the direction of the flange 22. At the bottom end opposite the flange 22, the valve body has a frustroconical shape terminating in a rounded tip.

The valve body 21 is inserted in the chamber 4 and its upper flange 22 is supported on a circumferential ledge 25 of the chamber 4.

Opposite the flange 22, the cover 2 has a cylindrical, circumferential projection 26 extending into the chamber 4 and abutting the top surface of the flange 22. Thus, the flange 22 is clamped between the ledge 25 and the projection 26 and is fixedly held in the chamber 4. At the same time, the flange 22 serves as a seal between the housing 1 and the cover 2.

The cover 2 has an opening 27 which is axial with the cylindrical projection 26 and with the valve body 21 and through which extends a valve actuation member consisting of an integral assembly of a cylindrical plunger 28, a shaft 29 and an actuating button 30. Shaft 29 is guided in opening 27 and is provided with a snap ring 31 in the shape of a radially protruding, annular ring lying in the transition region between the shaft 29 and plunger 28. The radially outward side of the ring is beveled with an angled edge tapering toward the plunger 28. At its lower, free end, the plunger 28 is frustoconical with a rounded tip 32.

The plunger 28 is introduced from the outside of the cover 2 into the opening 27 until the snap ring 31 snaps in behind the edge of the opening 27 due to the cylindrical opening of the projection 26 being somewhat larger in diameter than the opening 27. This secures the actuating member against being pulled axially out of the cover. The actuating knob 30 attached to the shaft 29 has a larger diameter than the shaft 29, forming an axial stop as it abuts the housing 2, to limit the degree of inward motion of the actuating member. The diameter of the plunger 28 is substantially equal to that of the cylindrical bore 23 of the valve body 21 so that a void is formed in the vicinity of the frustroconical front end 32. In the normal, unactuated position, the outside wall of the valve body 21 lies snugly against the inside wall of the chamber 4 over a large area of the chamber so that passage 5 between the chambers 3 and 4 is sealed off. Immediately adjacent to the passage 5, the wall 17 which separates the chambers 3 and 4 is angled downward toward the chamber 4 so that when fluid does flow, it can pass through the passage 5 past the projection 26 and flange 22.

In the normal, unactuated position, as shown in FIG. 1, the elastic properties of the material of the valve body urge it to contract and assume its basic shape so that the actuating member 30 is pushed as far upward in the direction of the cover 2 until the snap ring 31 makes contact with the cover. In that position, the wall of the valve body 21 is relatively thick so that it abuts the inside wall of chamber 4, thereby closing off the passage 5 which is the only inlet to the chamber 4.

Figure 2:
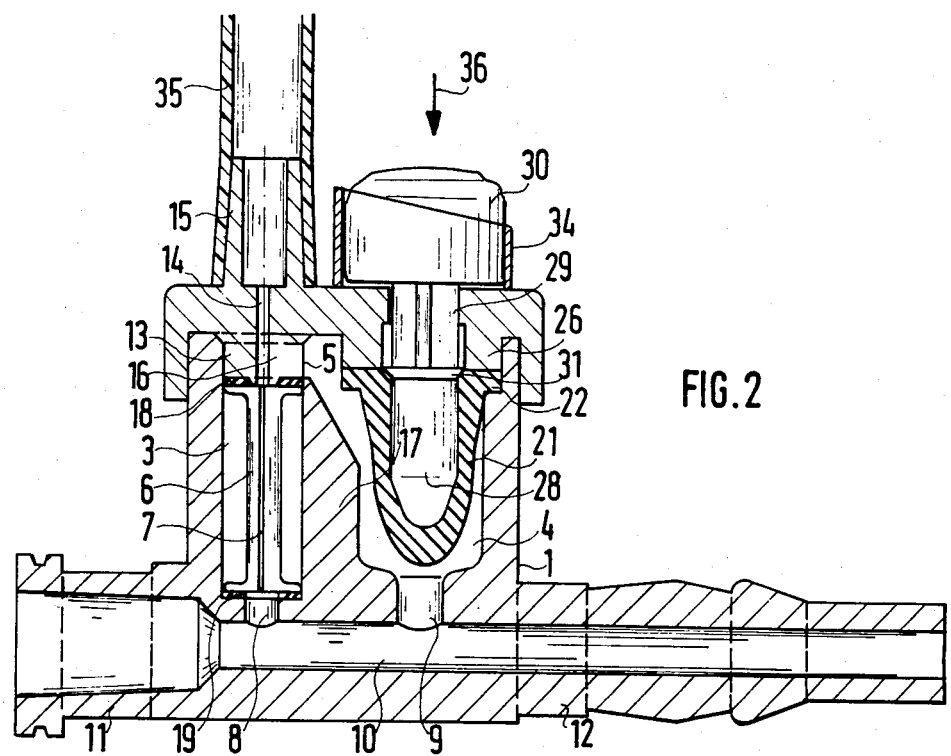
FIG. 2 is a crossectional view, similar to that of FIG. 1, but showing the actuation position with an opened rapid flushing passage.

If the actuating knob 30 is now depressed in the direction of the arrow 36, as shown in FIG. 2, plunger 28 stretches the valve body 21 and deforms it so as to make the wall of the valve body 21 thinner. In this process, the inside of the valve body snugly contacts the outside of the plunger 28 while the outside of the valve body is pulled away from the inside wall of the chamber 4 and thus opens a path from the passage 5 into the chamber 4 and through the opening 9. Hence, flushing fluid from a container (not shown) can now flow out of the tube 35 through the bore 14 and the transverse opening 16 to the passage 5 and through the chamber 4 and the opening 9 into the channel 10. The relatively large crossectional of opening of this flow path creates a "rapid flush" so that the entire flow control device can be de-aerated very quickly.

If the push button 30 is released from the position shown in FIG. 2, the elastic property of the valve body 21 urges the plunger 28 and hence the entire actuating member back into its normal rest position as shown in FIG. 1.

Attached to the cover 2 is a sleeve 34 coaxial with and partly surrounding the push button 30, and having an angled upper rim. This sleeve serves as a protection against unintentional actuation of the push button 30.

The present construction of the valve body and the actuating member achieves various benefits. The entire flow control device requires fewer parts and eliminates the need of a separate spring to force the actuating member back into its normal rest position. Additionally, the valve body serves as a sealing element for blocking the flow passage, as a retracting element and also as a sealing element for sealing the housing 1 with respect to the cover 2.

The frustroconical shape 24 at the lower, free end of the valve body 21 requires an excess of elastic material in that region. As a result, the lower part of the valve body 21 is only minimally deformed when the plunger 28 is depressed, causing the desired elongation of the side wall of the valve body. Moreover, this excess of material serves to reduce the filling volume of the chamber 4, thereby shortening the venting time.

It should also be noted that the invention is not limited to the exemplary embodiment shown. For example, the capillary bore may, as in U.S. Pat. No. 4,291,702, pass coaxially through the plunger 28, in which case the valve body must have an opening at its lower end. To prevent the closure of that opening in the normal, rest position, the plunger 28 may, for example, have a cylindrical extension with a capillary bore that is pushed through an opening in the tip of the valve body.

There has been disclosed heretofore the best embodiment of the invention presently comtemplated. However, it is to be understood that various changes and modification may be made thereto, without departing from the spirit of the invention.

What is claimed is:

1. A flow control device for use in fluid flow systems for pressure monitoring during blood pressure measurements, comprising a housing having at least one passage therethrough, said passage having an inlet and an outlet adapted for coupling to a catheter which is continuously flushed by the fluid, a capillary bore defining a non-closable first flow path from said inlet to said outlet, a closeable second flow path from said inlet to said outlet having a greater cross-sectional area than said first flow path, said second flow path comprising a chamber and a valve within said chamber having a valve body formed of elastically deformable material having a poriton positioned to press against the wall of said chamber to close off said second flow path, and a plunger movably coupled to said housing and positioned to distend and elongate said valve body portion within said chamber, thereby reducing the cross-sectional area of said valve body portion and causing said valve body portion to move away from said chamber wall to open said second flow path.

2. A flow control device as in claim 1, wherein said valve body is cylindrical in shape with a bore particularly extending into said valve body from one end thereof for receiving said plunger, an annular flange radially projecting from said one end of said valve body and positioned in said housing to retain said valve body dependingly supported from said housing.

3. A flow control device as in claim 2, wherein said valve body bore defines an interior cylindrical wall of the valve body and said plunger is located within said valve body bore and has a frustoconical tip on its distal end to thereby define a space between the exterior of said distal end of the plunger and the interior cylindrical wall of said valve body.

4. A flow control device as in claim 2, wherein both said plunger and said bore are of substantially equal cylindrical shape.

5. A flow control device as in claim 2, and comprising a cover for said housing, and an annular seat formed in said housing, said flange being clamped between said seat and said cover to help retain said valve body and to form a fluid seal between said housing and said cover.

6. A flow control device as in claim 2, wherein said valve body comprises a cylindrical annular wall between the exterior of the body and said bore, and a frustroconcial distal end, said distal end having a greater thickness of material than the thickness of said wall, whereby said wall will distend upon displacement of said plunger toward said distal end.

7. A flow control device as in claim 1, wherein both said chamber and said valve body are cylindrical in shape and said valve body has an outside diameter substantially equal to the inside diameter of said chamber, whereby in an undistended position said valve body blocks said second flow path.

8. A flow control device as in claim 1, and comprising a shaft coupled to said plunger, a beveled snap ring integrally connected between said shaft and said plunger for retaining said plunger in said housing.

9. A flow control device as in claim 8, and comprising a cover on said housing, an opening in said cover for suitable passage of said shaft, an annular ledge formed in said opening defining a seat for securely retaining said snap ring.

10. A flow control device as in claim 9, and comprising an actuating knob coupled to said shaft and projecting from said cover so as to be manipulatable externally of said cover.

11. A flow control device as in claim 10, wherein said actuating knob, said shaft, said plunger and said ring are integrally formed of plastic material.

12. A flow control device as in claim 1, wherein said first and second flow paths are substantially in parallel and separated by a median wall, each of said first and second flow paths having respective separate discharges into said outlet, a channel in said median wall connecting said second flow path to said first flow path, whereby said second flow path is coupled to the inlet through said first flow path.

13. A flow control device as in claim 12, wherein said channel is downwardly angled toward the outlet of said second flow path.

14. A flow control device as in claim 1, wherein said valve body material is silicon rubber.

* * * * *